United States Patent
Szczerba et al.

(10) Patent No.: US 11,325,531 B2
(45) Date of Patent: May 10, 2022

(54) SYSTEM FOR PROMOTING PASSENGER TRUST AND MITIGATING MOTION SICKNESS IN A VEHICLE

(71) Applicant: GM GLOBAL TECHNOLOGY OPERATIONS LLC, Detroit, MI (US)

(72) Inventors: Joseph F. Szczerba, Grand Blanc, MI (US); Jingyan Wan, Sterling Heights, MI (US); Omer Tsimhoni, Bloomfield Hills, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 280 days.

(21) Appl. No.: 16/389,349

(22) Filed: Apr. 19, 2019

(65) Prior Publication Data
US 2020/0331386 A1    Oct. 22, 2020

(51) Int. Cl.
| | |
|---|---|
| *B60Q 3/70* | (2017.01) |
| *G05D 1/02* | (2020.01) |
| *B60Q 9/00* | (2006.01) |
| *B60Q 3/80* | (2017.01) |
| *B60Q 5/00* | (2006.01) |
| *B60N 2/90* | (2018.01) |

(52) U.S. Cl.
CPC .................. *B60Q 3/80* (2017.02); *B60N 2/90* (2018.02); *B60Q 3/70* (2017.02); *B60Q 5/005* (2013.01); *B60Q 9/00* (2013.01); *G05D 1/0212* (2013.01); *B60N 2002/981* (2018.02)

(58) Field of Classification Search
CPC . B60Q 3/80; B60Q 3/70; B60Q 5/005; B60Q 9/00; B60Q 3/78; B60Q 3/74; B60N 2/90; B60N 2002/981; G05D 1/0212; A61M 21/00; B60K 35/00
See application file for complete search history.

(56) References Cited

U.S. PATENT DOCUMENTS

| | | | |
|---|---|---|---|
| 2011/0282130 A1* | 11/2011 | Krueger | G02B 27/017 600/27 |
| 2017/0253181 A1* | 9/2017 | Choi | B60K 35/00 |
| 2017/0253254 A1* | 9/2017 | Sweeney | B60R 1/00 |
| 2018/0229988 A1* | 8/2018 | Gault | B66F 9/24 |
| 2019/0357834 A1* | 11/2019 | Aarts | G08B 21/06 |

* cited by examiner

*Primary Examiner* — Ig T An
(74) *Attorney, Agent, or Firm* — Cantor Colburn LLP

(57) ABSTRACT

A system for promoting passenger trust and to mitigate motion sickness in a vehicle may include a first sensor structured to detect an operational status of the vehicle, a processor operably coupled to the first sensor; and a subliminal sensory system operably coupled to the processor. The processor may be structured to control the subliminal sensory system to subliminally provide information about the operational status of the vehicle to a passenger.

3 Claims, 22 Drawing Sheets

SYSTEM FOR PROMOTING PASSENGER TRUST AND MITIGATING MOTION SICKNESS IN A VEHICLE

INTRODUCTION

The subject disclosure relates to a system and method for measuring passenger satisfaction in an autonomous vehicle, increasing passenger satisfaction in an autonomous vehicle, and adjusting driving behavior of an autonomous vehicle based on passenger satisfaction.

Developments in autonomous vehicle technology may allow greater access to autonomous vehicles by the public. However, as with many new technologies, there may initially be a lack of trust by passengers in the driving capabilities of autonomous vehicles. Additionally, passengers may become frustrated by the driving operation of an autonomous vehicle, especially if the passenger is unaware of the data with which the autonomous vehicle is making decisions. These issues of lack of trust, lack of satisfaction, and passenger frustration may delay adoption of autonomous vehicle technology by the public.

Whether in an autonomous vehicle or a conventional vehicle, passengers may suffer from motion sickness when their sensory perceptions are out of sync with the apparent forces felt by their body from the operation of a vehicle. This is particularly true if the passenger is not concentrating on the operation of the vehicle, such as when a passenger is reading a book, operating a personal device, or conversing with another passenger.

Accordingly, it may be desirable to provide a system that can enhance user trust and satisfaction regarding operation of the vehicle, as well as mitigating instances of motion sickness, by providing sensory cues regarding anticipated or imminent forces to be felt by the passenger. It may further be desirable for these sensory cues to be subliminal, subconscious, or precognitive, so as not to startle a passenger or distract them from other activities.

SUMMARY

In one exemplary embodiment, a system for promoting passenger trust and to mitigate motion sickness in a vehicle may include a first sensor structured to detect an operational status of the vehicle, a processor operably coupled to the first sensor, and a subliminal sensory system operably coupled to the processor. The processor may be structured to control the subliminal sensory system to subliminally provide information about the operational status of the vehicle to a passenger.

In another exemplary embodiment, the subliminal sensory system may be a lighting system provided in an interior of the vehicle. The processor may be structured to control color, intensity, or apparent motion of the lighting system to provide information about the operational status of the vehicle to the passenger.

In another exemplary embodiment, the processor may be structured to control the color, the intensity, or the apparent motion of the lighting system to provide a visual representation of an anticipated force on the passenger.

In another exemplary embodiment, the system may further include a second sensor structured to detect a driving environment of the vehicle. The processor may be structured to control the color, the intensity, or the apparent motion of the lighting system to provide a visual representation of an object proximate to the vehicle based on the driving environment detected by the second sensor.

In another exemplary embodiment, the subliminal sensory system may be a sound system provided in an interior of the vehicle. The processor may be structured to control pitch, volume, or apparent direction of a source of an output of the sound system to provide information about the operational status of the vehicle to the passenger.

In another exemplary embodiment, the sound system may be a set of speakers provided in the vehicle.

In another exemplary embodiment, the sound system may be a personal sound device worn by the passenger and structured to wirelessly communicate with the processor.

In another exemplary embodiment, the processor may be structured to control the pitch, the volume, or the apparent direction of the output of sound system to provide an audible representation of an anticipated force on the passenger.

In another exemplary embodiment, the system may include a second sensor structured to detect a driving environment of the vehicle. The processor may be structured to control the control the pitch, the volume, or the apparent direction of the output of sound system to provide an audible representation of an object proximate to the vehicle.

In another exemplary embodiment, the subliminal sensory system may be a haptic system provided in the vehicle. The processor may be structured to control operation of the haptic system to provide information about the operational status of the vehicle to the passenger.

In another exemplary embodiment, the haptic system comprises a stimulation device provided in a seat of the vehicle.

In one exemplary embodiment, a system for promoting passenger trust and to mitigate motion sickness in a vehicle having an automated driving system to autonomously operate the vehicle may include a first sensor to detect a driving environment of the vehicle. The first sensor may be operably coupled to the automated driving system. The system may further include a processor operably coupled to the first sensor and the automated driving system, and the processor may be configured to calculate a vehicle path plan based on the driving environment of the vehicle and local infrastructure information. The system may further include a subliminal sensory system operably coupled to the processor. The processor may be structured to control the subliminal sensory system to subliminally provide information about the operational status of the vehicle to a passenger based on the vehicle path plan.

In another exemplary embodiment, the processor may structured to control the subliminal sensory system to provide a visual representation of an anticipated force on the passenger based on the vehicle path plan.

In another exemplary embodiment, the processor may be structured to control the subliminal sensory system to provide a representation of an object proximate to the vehicle based on the driving environment detected by the second sensor.

In another exemplary embodiment, the subliminal sensory system may be a lighting system provided in an interior of the vehicle. The processor may be structured to control color, intensity, or apparent motion of the lighting system to provide information about the operational status of the vehicle to the passenger.

In another exemplary embodiment, the subliminal sensory system may be a sound system provided in an interior of the vehicle. The processor may be structured to control pitch, volume, or apparent direction of an output of the sound system to provide information about the operational status of the vehicle to the passenger.

In another exemplary embodiment, the subliminal sensory system may be a haptic system provided in the vehicle. The processor may be structured to control operation of the haptic system to provide information about the operational status of the vehicle to the passenger.

In one exemplary embodiment, a system for promoting passenger trust and to mitigate motion sickness in a vehicle may be used in conjunction with a personal electronic device of a user. The system may include a first sensor structured to detect an operational status of the vehicle, and a processor operably coupled to the first sensor. The processor may be structured to wirelessly communicate with the personal electronic device and control the personal electronic device to subliminally provide information about the operational status of the vehicle to a passenger.

In another exemplary embodiment, the processor may be structured to control a display of the personal electronic device to show a graphic around an outer periphery of the display. The processor may be structured to control the color, the intensity, or the apparent motion of the graphic to provide a visual representation of an anticipated force on the passenger.

In another exemplary embodiment, the system may further include a second sensor structured to detect a driving environment of the vehicle. The processor may be structured to control a display of the personal electronic device to show a graphic around an outer periphery of the display. The processor may be structured to control the color, the intensity, or the apparent motion of the lighting system to provide a visual representation of an object proximate to the vehicle based on the driving environment detected by the second sensor.

The above features and advantages, and other features and advantages of the disclosure are readily apparent from the following detailed description when taken in connection with the accompanying drawings.

BRIEF DESCRIPTION OF THE DRAWINGS

Other features, advantages and details appear, by way of example only, in the following detailed description, the detailed description referring to the drawings in which.

DETAILED DESCRIPTION

Figure 1:
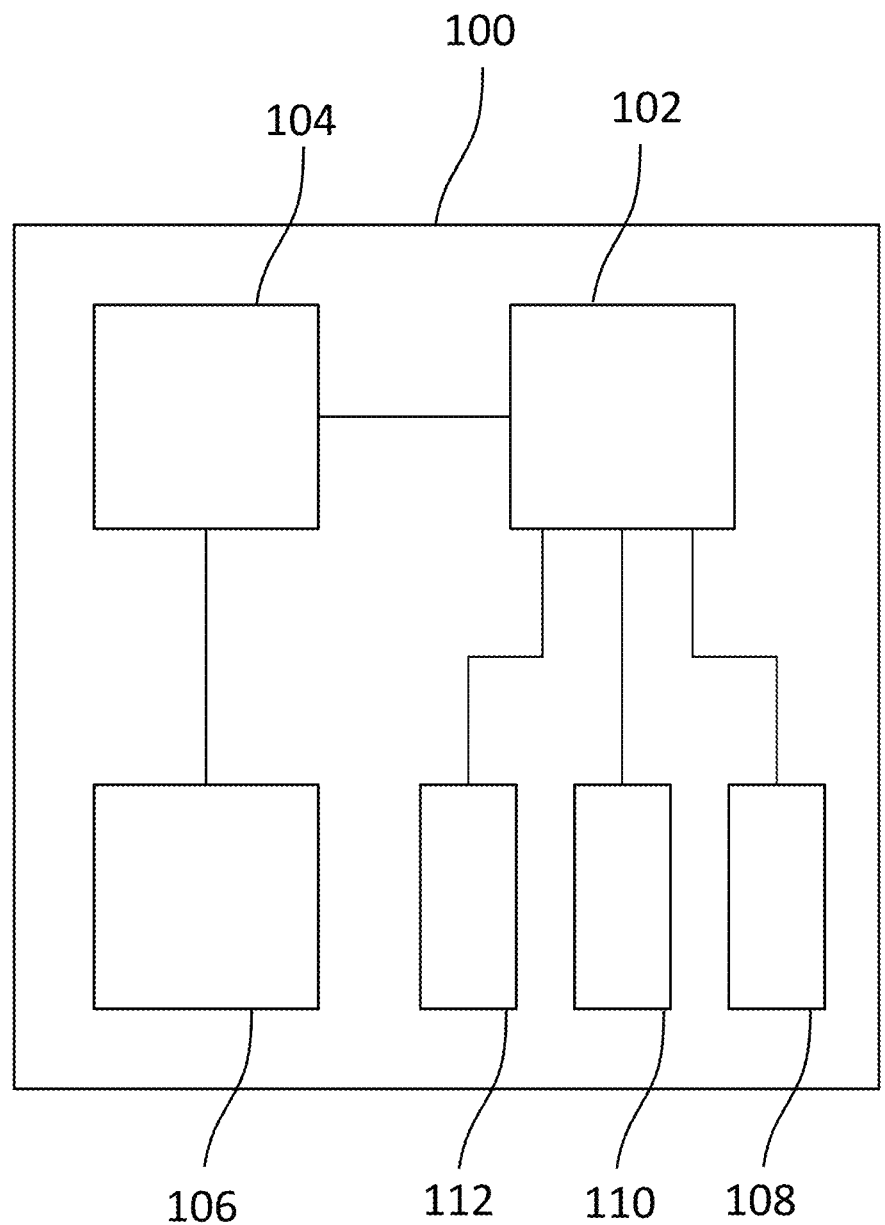
FIG. 1 is a schematic diagram illustrating an exemplary embodiment of a system for promoting passenger trust and mitigating motion sickness in a vehicle.

The following description is merely exemplary in nature and is not intended to limit the present disclosure, its application or uses. It should be understood that throughout the drawings, corresponding reference numerals indicate like or corresponding parts and features. As used herein, the term module refers to processing circuitry that may include an application specific integrated circuit (ASIC), an electronic circuit, a processor (shared, dedicated, or group) and memory that executes one or more software or firmware programs, a combinational logic circuit, and/or other suitable components that provide the described functionality.

FIG. 1 shows an exemplary embodiment of a system 100 for promoting passenger trust and mitigating motion sickness in a vehicle. System 100 may include a first sensor 102, a processor 104, and a subliminal sensory system 106. First sensor 102 may be operably coupled to processor 104 and structured to detect an operational status of the vehicle. For example, first sensor 102 may be operably connected to an accelerator 108 and structured to detect an acceleration force of the vehicle. Alternatively, first sensor 102 may be connected to a brake system 110 an structured to detect a braking maneuver of the vehicle. Alternatively, first sensor 102 may be connected a steering system 112 and structured to calculate an apparent centrifugal force acting on a vehicle based on an amount of steering and a velocity of the vehicle. Accelerator 108, brake system 110, and steering system 112 may be controlled by a driver or controlled by an automated driving system. It will be understood that the accelerator 108, brake system 110, and steering system 112 are included as illustrative examples, and the first sensor is not limited to measuring only these systems.

Processor 104 may be operably connected to first sensor 102 and subliminal sensory system 106, and may be structured to control an output of subliminal sensory system 106 to subliminally provide information about the operational status of the vehicle to the passenger. At least an exemplary embodiment of subliminal sensory system 106 will be discussed in detail below.

In the present context, the term subliminal may refer to an output that may be perceived by the passenger and affect the passenger's physiology, behavior, or perception of the vehicle's motion, without requiring active and conscious recognition of the output by the passenger. It will be understood that use of the word subliminal does not require that the output must absolutely be below a conscious recognition level of the passenger, merely that the output can affect the passenger even if the output is not consciously recognized by the passenger.

FIGS. 2-8 show an exemplary embodiment of subliminal sensory system 106 described above with reference to FIG. 1.

Figure 2:
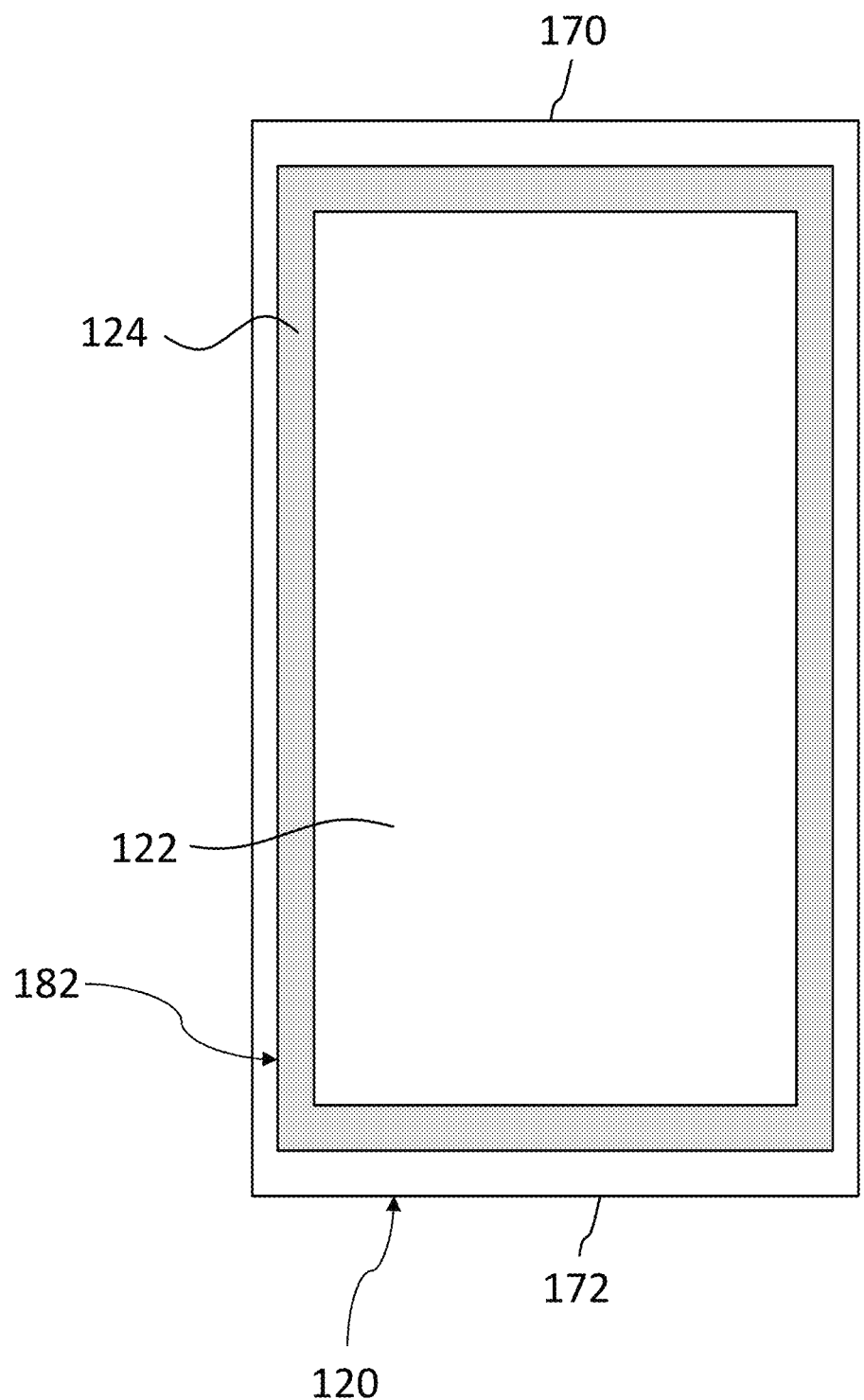
FIG. 2 is a schematic diagram of an exemplary embodiment of a lighting system in a vehicle.

In an exemplary embodiment shown in FIG. 2, a subliminal sensory system 106 embodied as a lighting system 182 may be a continuous string light 124 provided around an interior cabin 122 of vehicle 120.

The lighting elements forming the lighting system 182 may be LED elements, incandescent elements, or other suitable types of lighting elements for use within an interior cabin 122 of a vehicle 120. Processor 104 may be configured to control color, intensity, or apparent motion of the lighting system 182 to provide information about the operational status of the vehicle 120 to the passenger.

Figure 9:
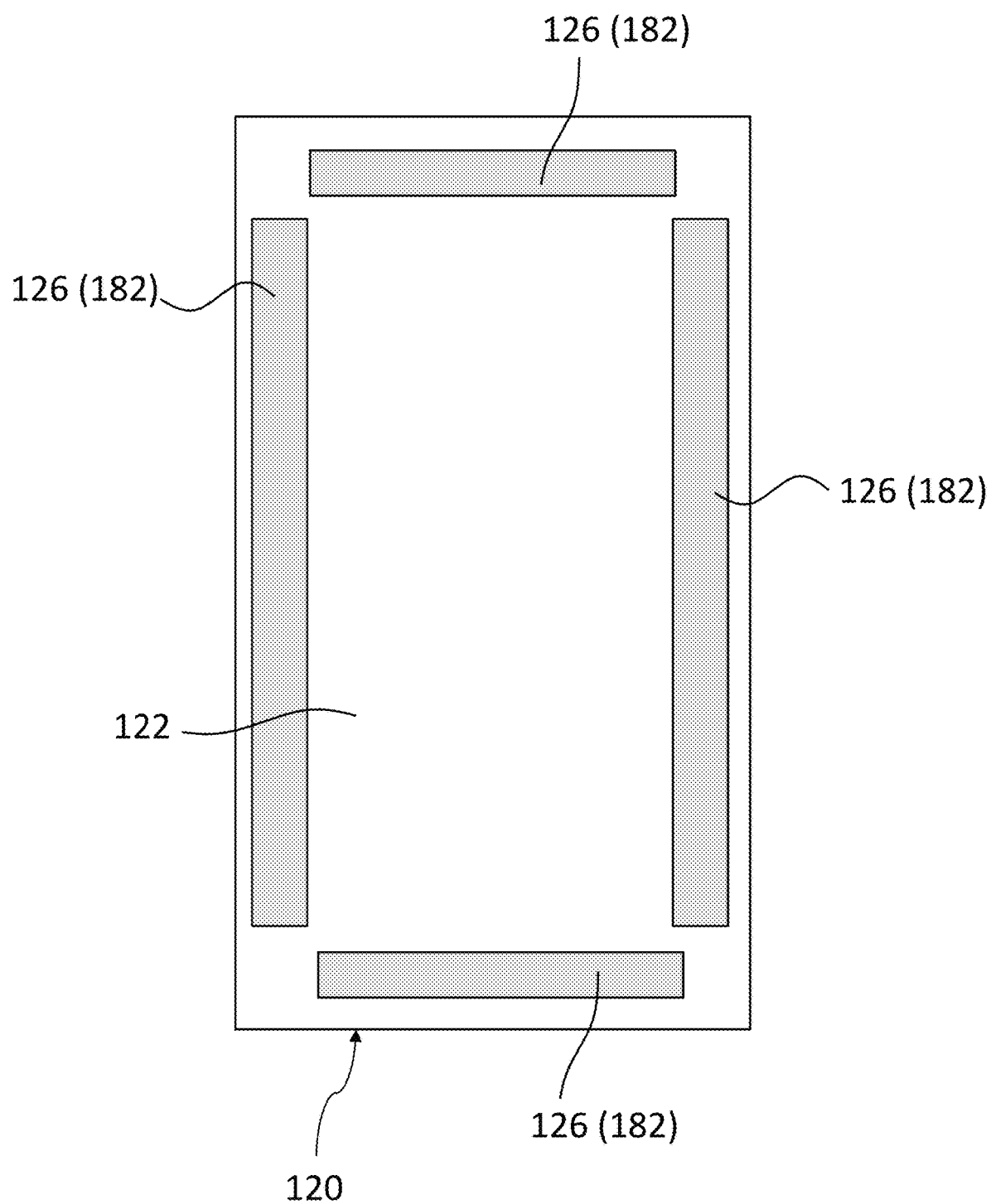
FIG. 9 is a schematic diagram of an exemplary embodiment of a lighting system in a vehicle.
Figure 10:
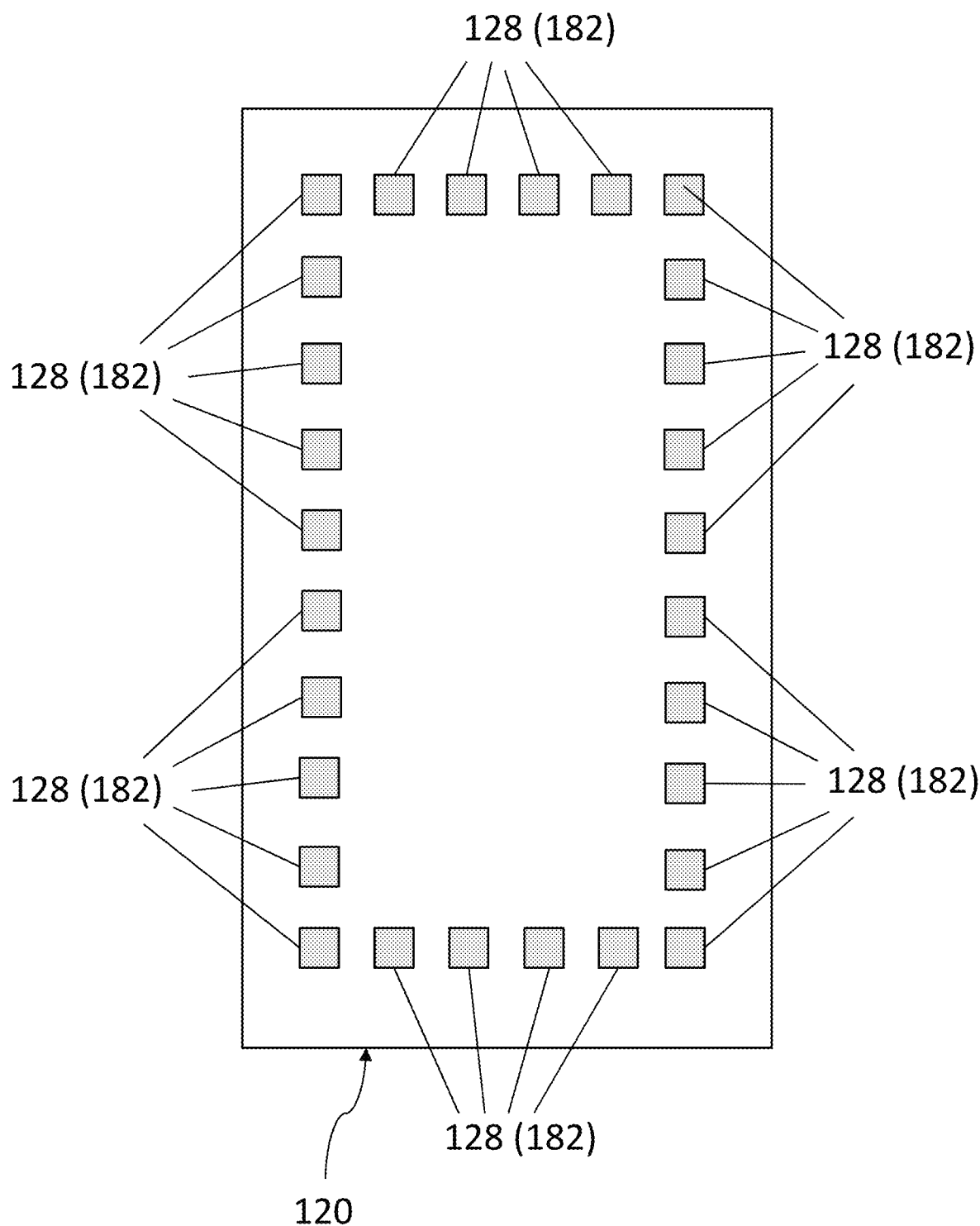
FIG. 10 is a schematic diagram of an exemplary embodiment of a lighting system in a vehicle.
Figure 11:
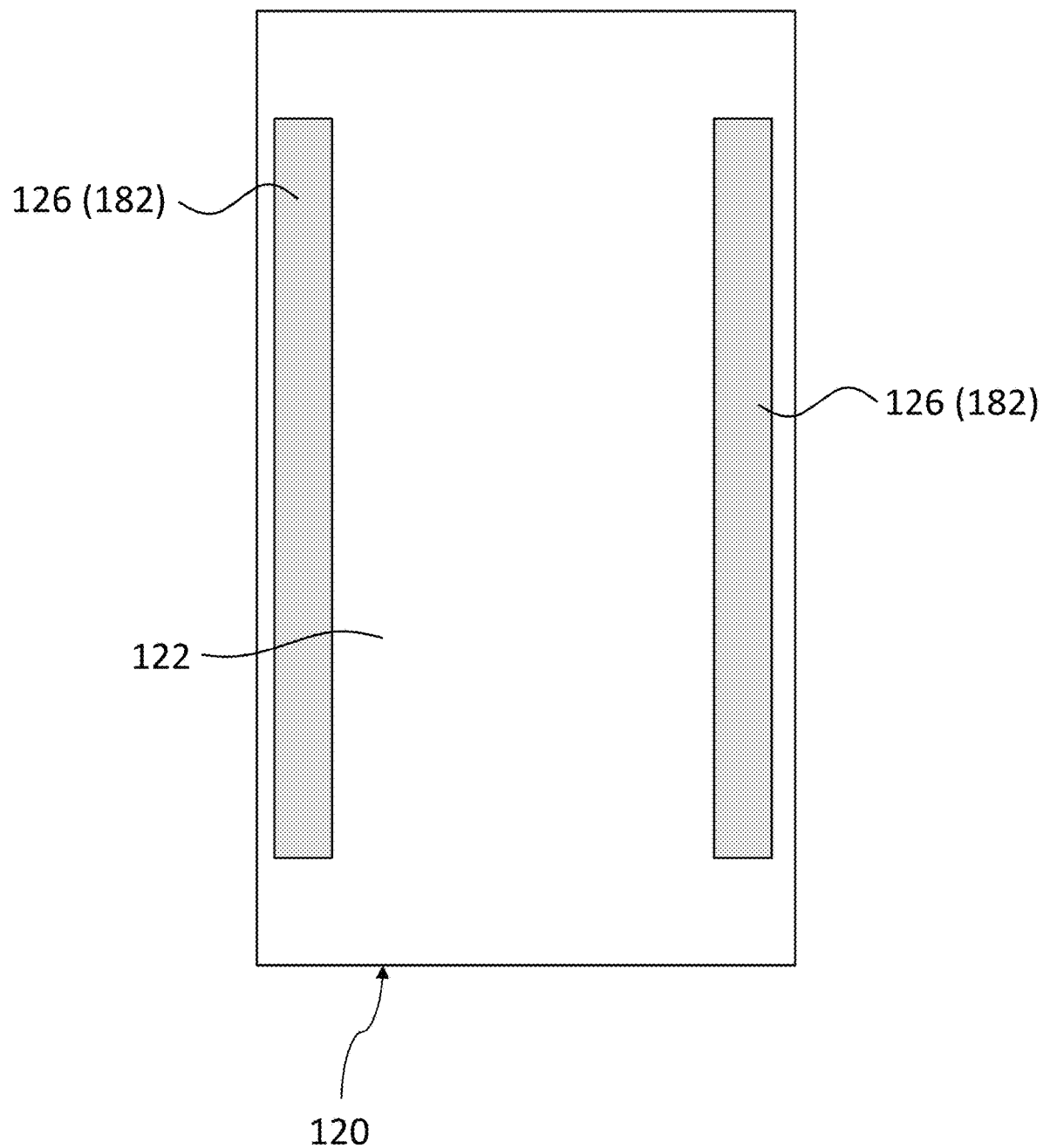
FIG. 11 is a schematic diagram of an exemplary embodiment of a lighting system in a vehicle.

It will be understood that the lighting system 182 is not limited to structure shown in FIG. 2, and instead may take a variety of forms. For example, FIG. 9 shows an exemplary embodiment where the lighting system 182 is provided as a series of separate lighting segments 126. Additionally, FIG. 10 shows an exemplary embodiment of the lighting system 182 implemented as a series of discrete lighting elements 128. It will also be understood that it is not necessary for the lighting system 182 to completely encompass the entire periphery of the interior cabin 122 of vehicle 120. For example, FIG. 11 shows an exemplary embodiment in which the lighting system 182 is implemented as two lighting segments 126 running along the sides of interior cabin 122 of vehicle 120.

The operation of processor 104 controlling the lighting system 182 will be described below with reference to string light 124 with reference to FIGS. 2-8, but it will be also understood that a similar effect can be achieved by coordinated control of the light segments 126 in FIGS. 9 and 11 or discrete lighting elements 128 in FIG. 10.

FIG. 2 shows an exemplary embodiment in which vehicle 120 is traveling at a constant rate of speed. In this condition, no apparent force would be felt by a passenger in the interior cabin 122 of vehicle 120. Accordingly, processor 104 controls light string 124 to maintain a static color and intensity throughout light string 124, as indicated by the constant shading.

Figure 3:
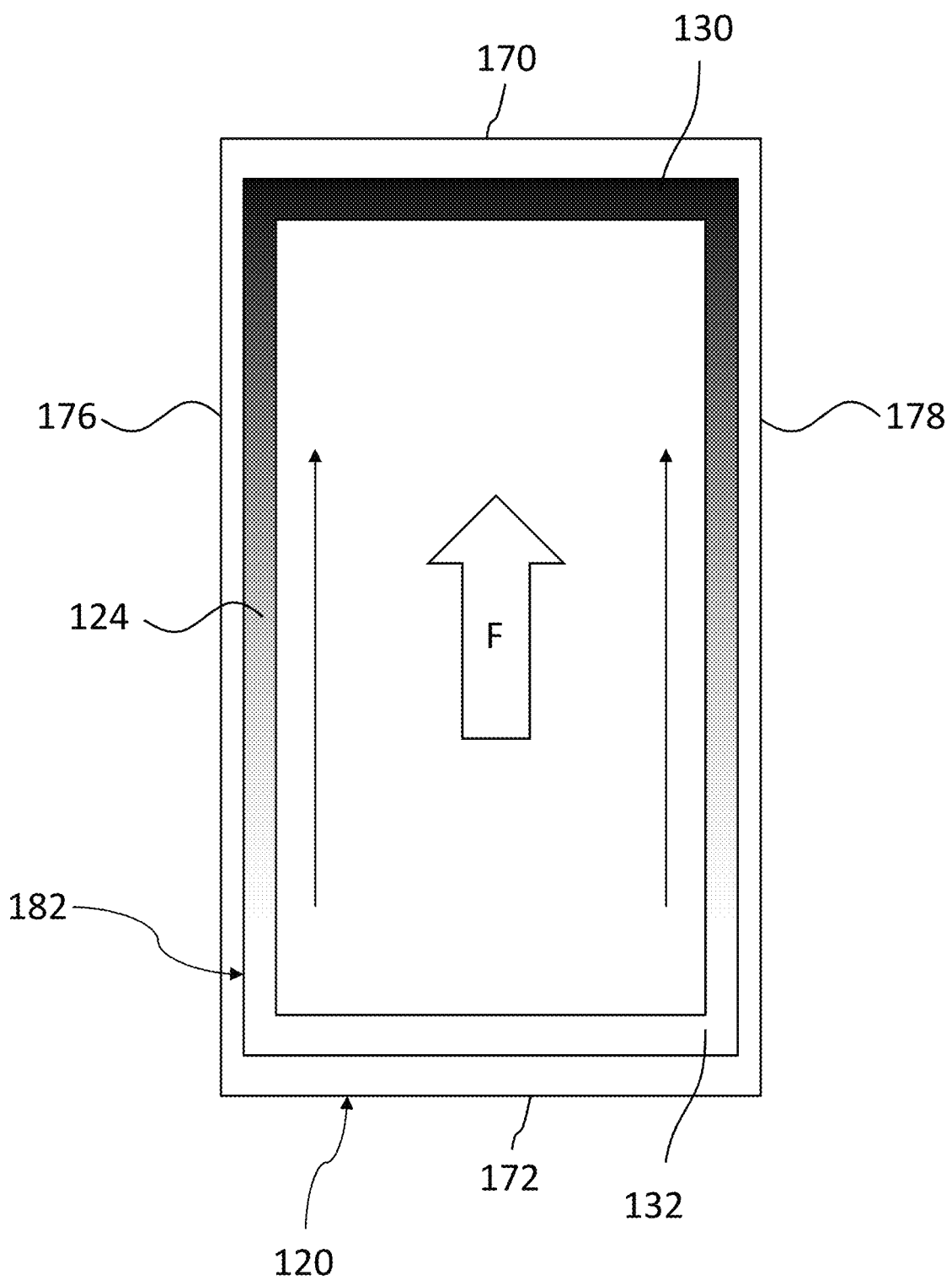
FIG. 3 is a schematic diagram of an exemplary embodiment of a lighting system in a vehicle.

FIG. 3 shows an exemplary embodiment of the operation of lighting system 182 when vehicle 120 brakes. When vehicle 120 brakes, the apparent force "F" on the passenger (due to the passenger's inertia) is toward the front 170 of vehicle 120. Accordingly, processor 104 (see FIG. 1) controls light string 124 to create a simulated motion of more intense light moving toward the front 170 of vehicle 120. The arrows in FIG. 3 represent the force "F" and the direction of the simulated motion of the light in light string 124. The darkly shaded region 130 indicates an area of high intensity light, while lightly shaded region 132 indicates an area of low intensity light. In the embodiment of FIG. 3, the animation and intensity of the light in light string 124 is intended to mimic or simulate the concept of a fluid provided in a tube corresponding to the string light 124. In this concept, when the vehicle brakes, the inertia of the fluid would cause it to flow toward, and collect in, the front 170 of the vehicle 120, corresponding to the high intensity light represented by darkly shaded region 130. In contrast, the fluid's inertia would cause it to flow away from a rear 172 of the vehicle 120, corresponding to the low intensity light represented by lightly shaded region 132.

Figure 4:
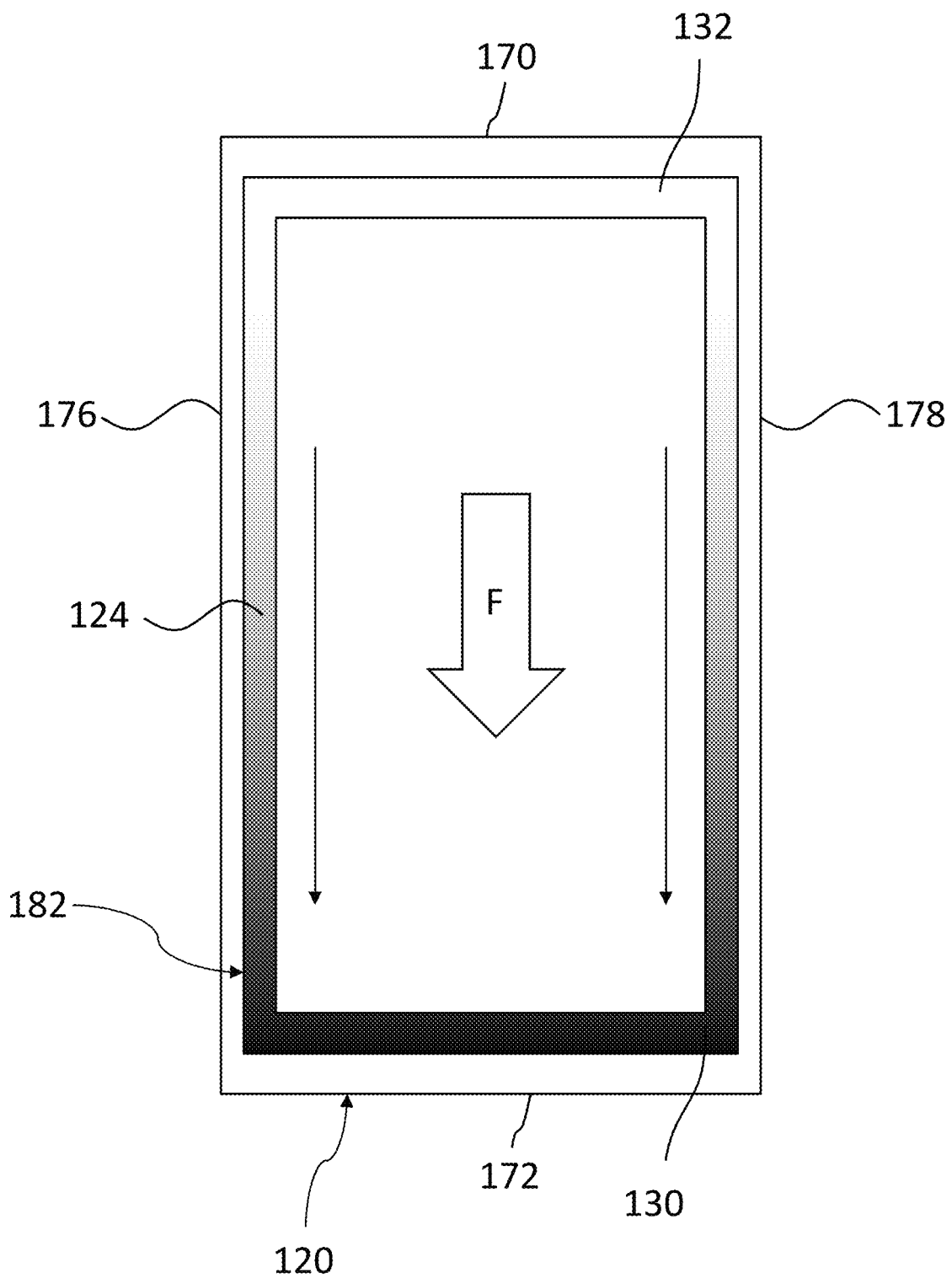
FIG. 4 is a schematic diagram of an exemplary embodiment of a lighting system in a vehicle.

FIG. 4 shows an exemplary embodiment of the operation of light string 124 when vehicle 120 accelerates. When vehicle 120 accelerates, the apparent force "F" on the passengers is toward a rear 172 of vehicle 120. Accordingly, processor 104 controls light string 124 to create a simulated motion of more intense light moving toward the rear 172 of vehicle 120. The arrows in FIG. 4 represent the force "F" and the direction of simulated motion of the light in light string 124. The darkly shaded region 130 indicates an area of high intensity light, while lightly shaded region 132 indicates an area of low intensity light. Similar to the embodiment shown in FIG. 3, the animation and intensity of the light in light string 124 is intended to mimic or simulate the concept of a fluid provided in a tube corresponding to the string light 124. In the case of FIG. 4, however, the fluid (i.e., high intensity light) gathers in darkly shaded region 130 in the rear 172 of vehicle 120 due the acceleration thereof.

Figure 5:
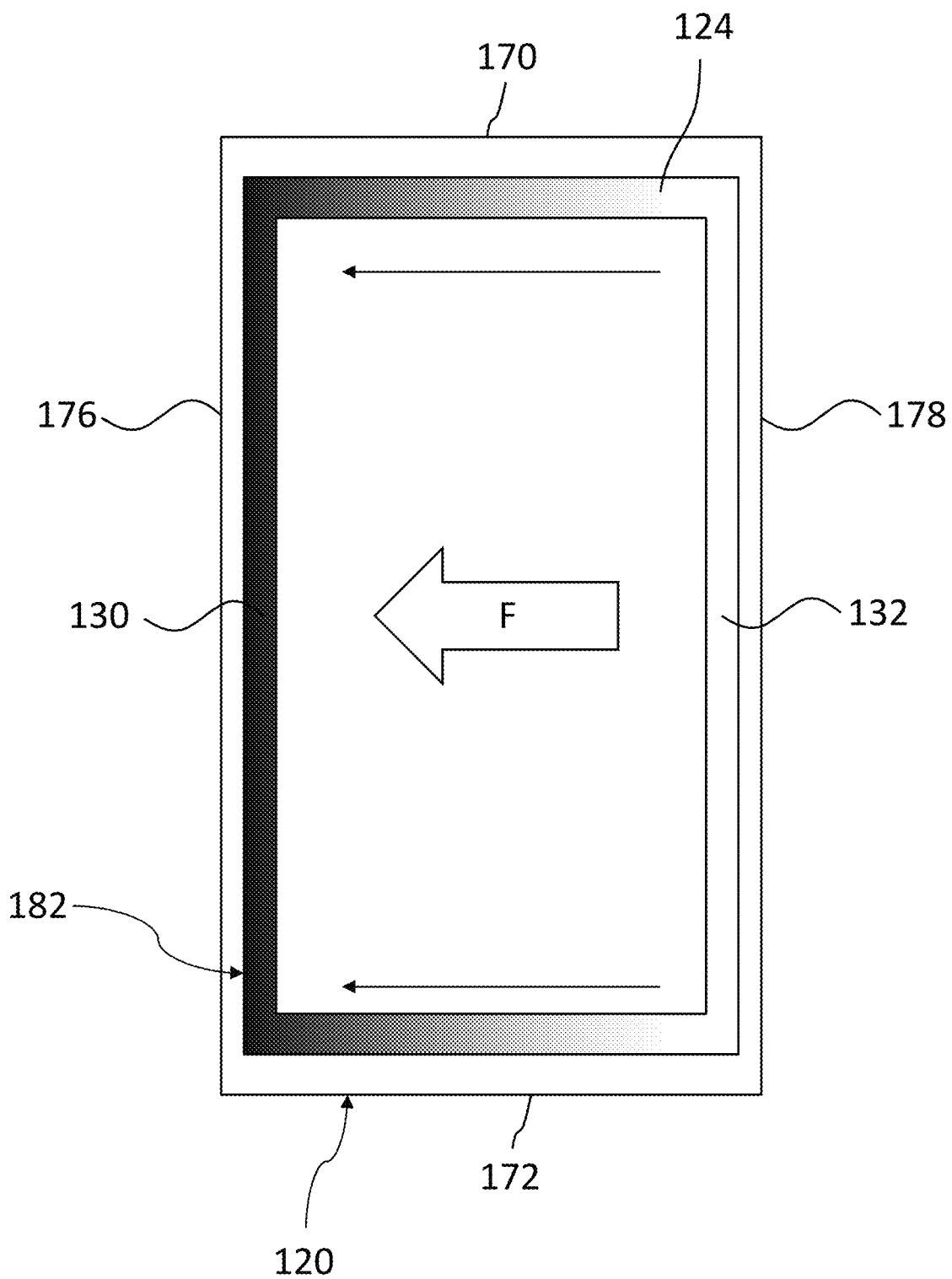
FIG. 5 is a schematic diagram of an exemplary embodiment of a lighting system in a vehicle.

FIG. 5 shows an exemplary embodiment of the operation of light string 124 when vehicle 120 turns to the right. When vehicle 120 turns to the right, the apparent force "F" felt by the passengers is an apparent centrifugal force to the left side 176 of the vehicle (i.e., the outside of the turn). Accordingly, processor 104 controls light string 124 to create a simulated motion of more intense light moving toward the left side 176 of vehicle 120. The arrows in FIG. 5 represent the force and the direction of simulated motion of the light in light string 124. Darkly shaded region 130 indicates an area of high intensity light, while lightly shaded region 132 indicates an area of low intensity light. Similar to the embodiments shown in FIGS. 3 and 4, the animation and intensity of the light in light string 124 is intended to mimic or simulate the concept of a fluid provided in a tube corresponding to the string light 124. In the case of FIG. 5, however, the fluid (i.e., high intensity light) gathers in darkly shaded region 130 to the left side of vehicle 120 due to the right turn thereof.

Figure 6:
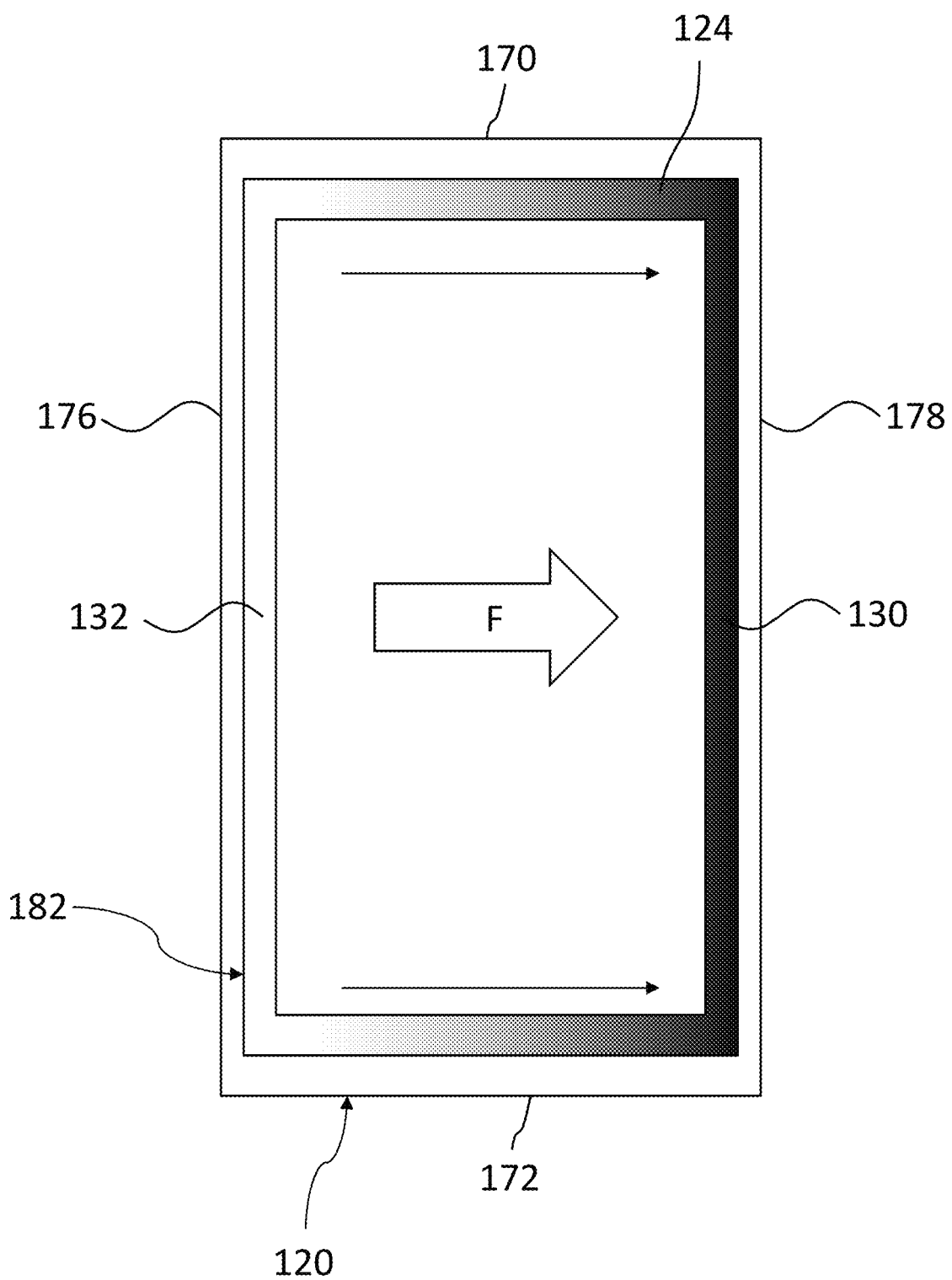
FIG. 6 is a schematic diagram of an exemplary embodiment of a lighting system in a vehicle.

FIG. 6 shows an exemplary embodiment of the operation of light string 124 when vehicle 120 turns to the left. When vehicle 120 turns to the left, the apparent force felt by the passenger is an apparent centrifugal force "F" to the right side 178 of the vehicle (i.e., the outside of the turn). Accordingly, processor 104 controls light string 124 to create a simulated motion of more intense light moving toward the right side 178 of vehicle 120. The arrows in FIG. 6 represent the direction of simulated motion of the light in light string 124. Darkly shaded region 130 indicates an area of high intensity light, while lightly shaded region 132 indicates an area of low intensity light. Similar to the embodiments shown in FIGS. 3-5, the animation and intensity of the light in light string 124 is intended to mimic or simulate the concept of a fluid provided in a tube corresponding to the string light 124. In the case of FIG. 6, however, the fluid (i.e., high intensity light) gathers in darkly shaded region 130 to the right side 178 of vehicle 120 due to the left turn thereof.

It will also be understood that the gradient of the light intensity and speed of animation of the light in light string 124 can be used to provide an indication of the magnitude of the braking, acceleration, or turning of vehicle 120.

Figure 7:
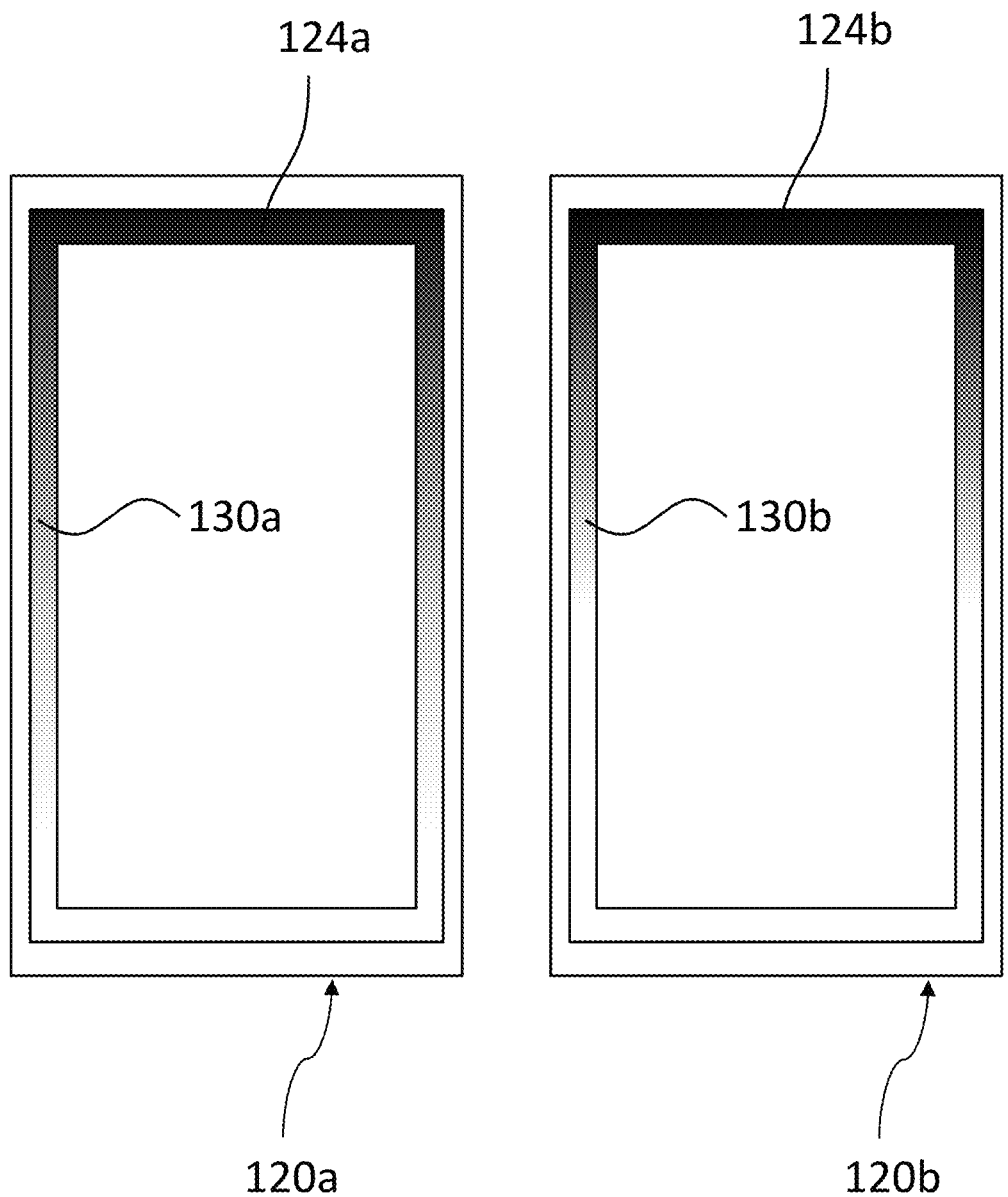
FIG. 7 is a comparative schematic diagram of an exemplary embodiment of a lighting system in a vehicle.

For example, FIG. 7 shows a comparison between two embodiments in which braking is applied to a vehicle. In vehicle 120a, a gradual braking is being applied. In contrast, a more severe braking is being applied in vehicle 120b. Accordingly, the gradient of light intensity in light string 124a is more gradual, as indicated by the shading 130a in FIG. 7. In contrast, the gradient of light intensity in light string 124b is sharper and more severe, as indicated by the shading 130b in FIG. 14. The sharper gradient in light string 124b is an indication of the stronger braking force being applied in vehicle 120b.

Figure 18:
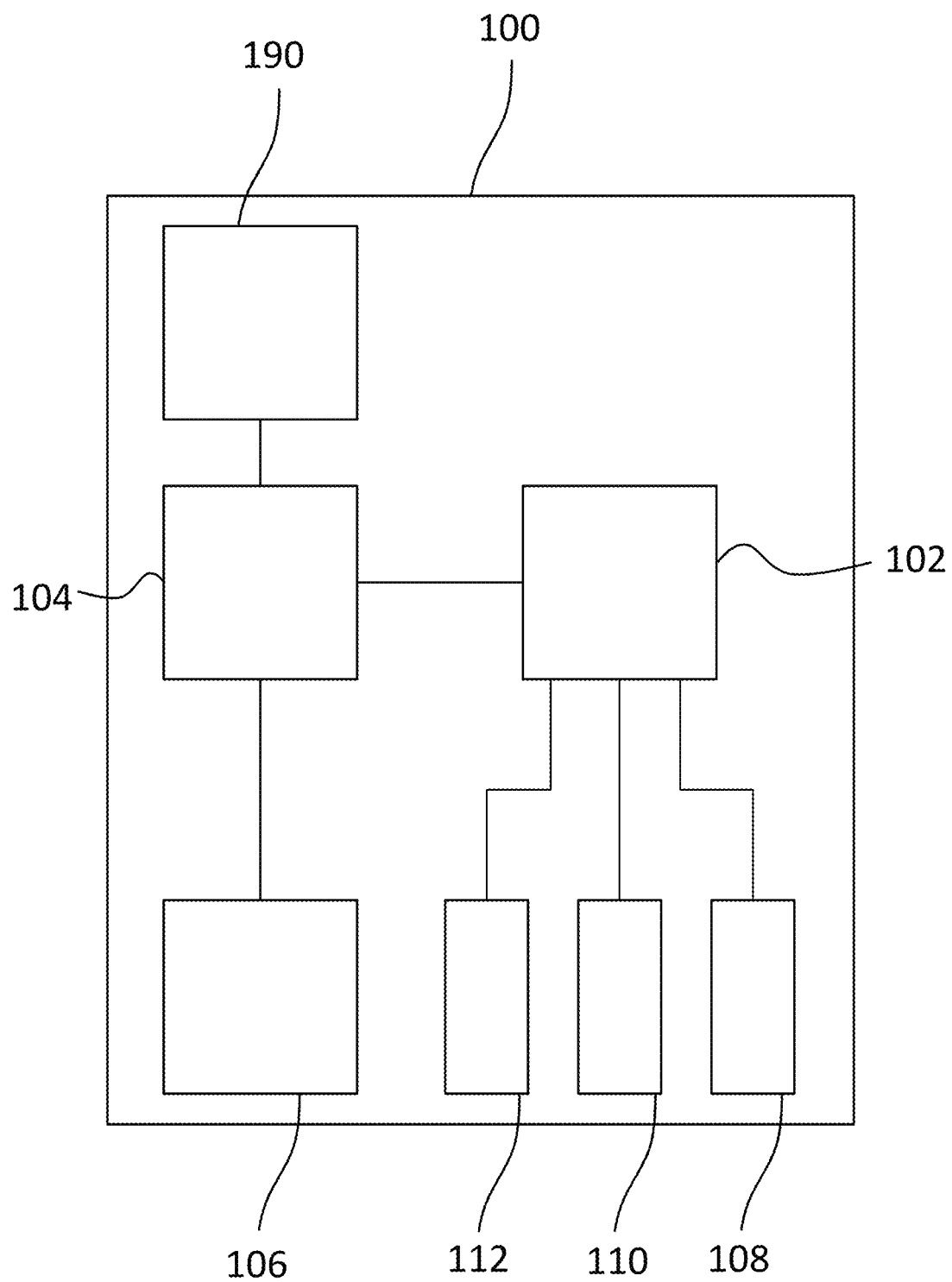
FIG. 18 is a schematic diagram illustrating an exemplary embodiment of a system for promoting passenger trust and mitigating motion sickness in a vehicle.
Figure 19:
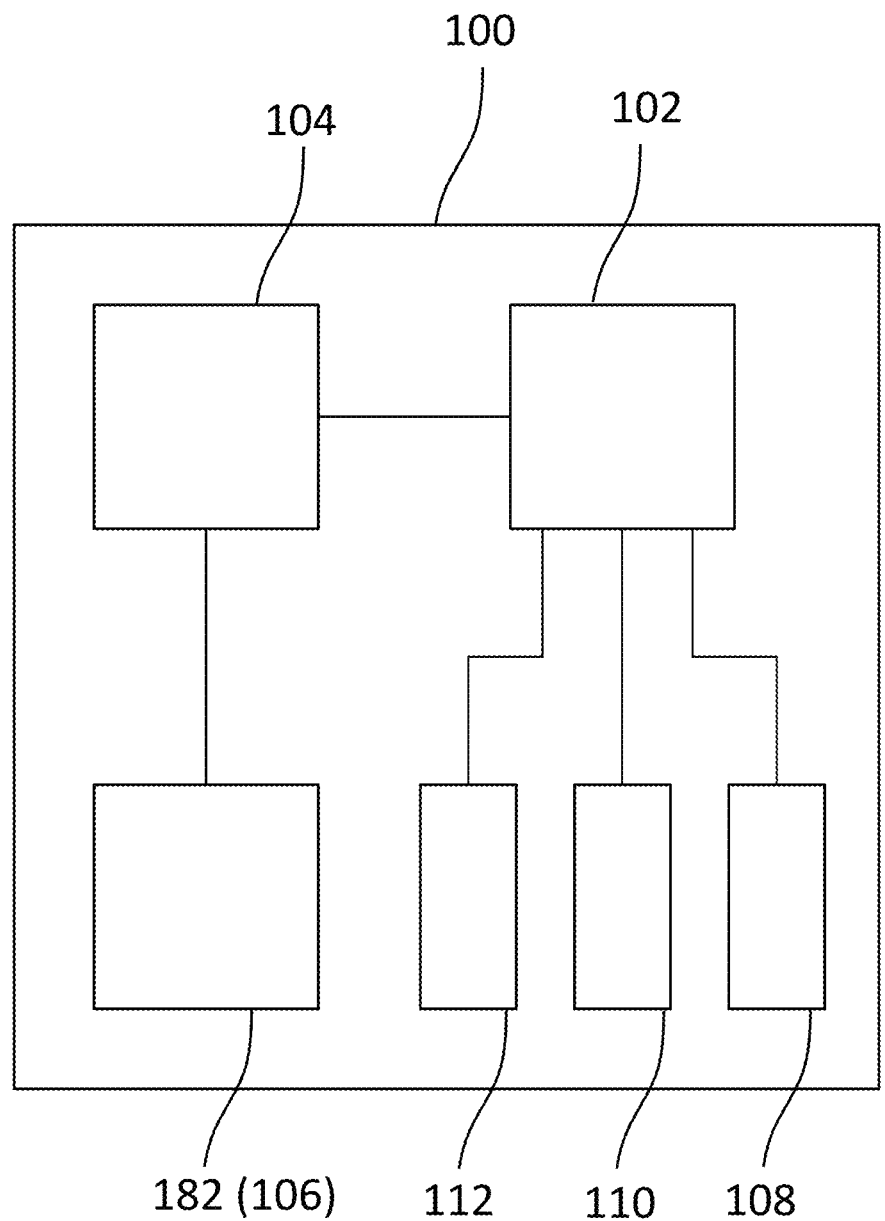
FIG. 19 is a schematic diagram illustrating an exemplary embodiment of a system for promoting passenger trust and mitigating motion sickness in a vehicle.

It will also be understood that light string 124 may be controlled to provide additional information using varying colors. For example, shown in FIG. 18, a vehicle may include a second sensor 190 structured to detect a driving environment of the vehicle, and, as exemplary embodiments, second sensor 190 may include a camera, Radio Detection and Ranging (RADAR) system, Light Detection and Ranging (LIDAR) system, or any combination of these systems. If processor 104 is operably connected to a sensor such as second sensor 190, processor 104 can use the input from the second sensor 190 to control lights 124 to provide information about the driving environment, such as nearby objects, to the passenger.

Figure 8:
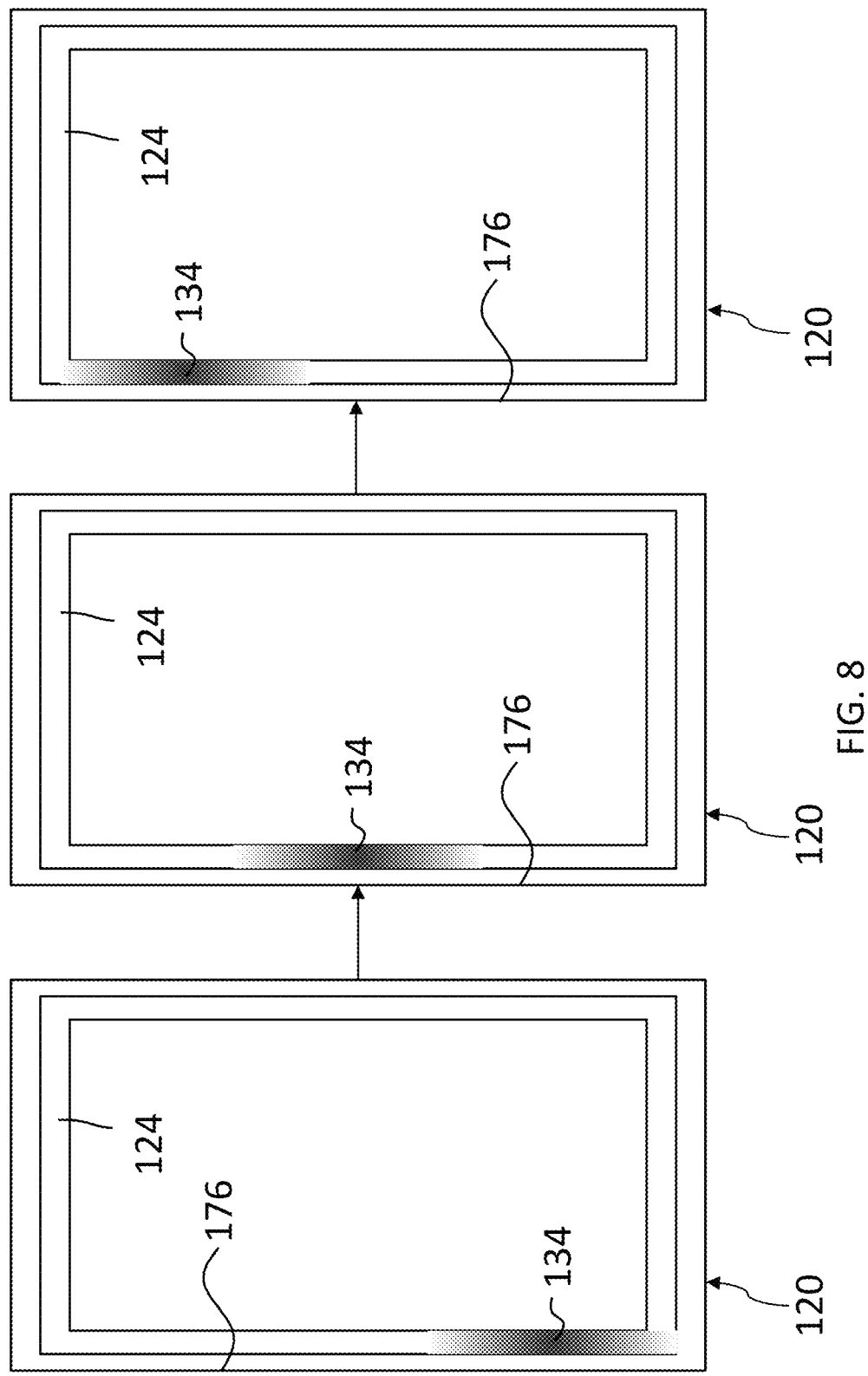
FIG. 8 is a sequential schematic diagram of an exemplary embodiment of a lighting system in a vehicle.

FIG. 8 shows an exemplary embodiment where processor 104 controls light string 124 uses color, motion, and/or brightness to inform passengers of a nearby object, such as a passing car. For example, a differently colored area (represented by shaded area 134 in FIG. 8) in string light 124 may be used to indicate the relative position of a nearby car. The progression of drawings from left to right in FIG. 8 indicates the movement of shaded area 134 as a second vehicle passes vehicle 120 on the left side 176.

Figure 12:
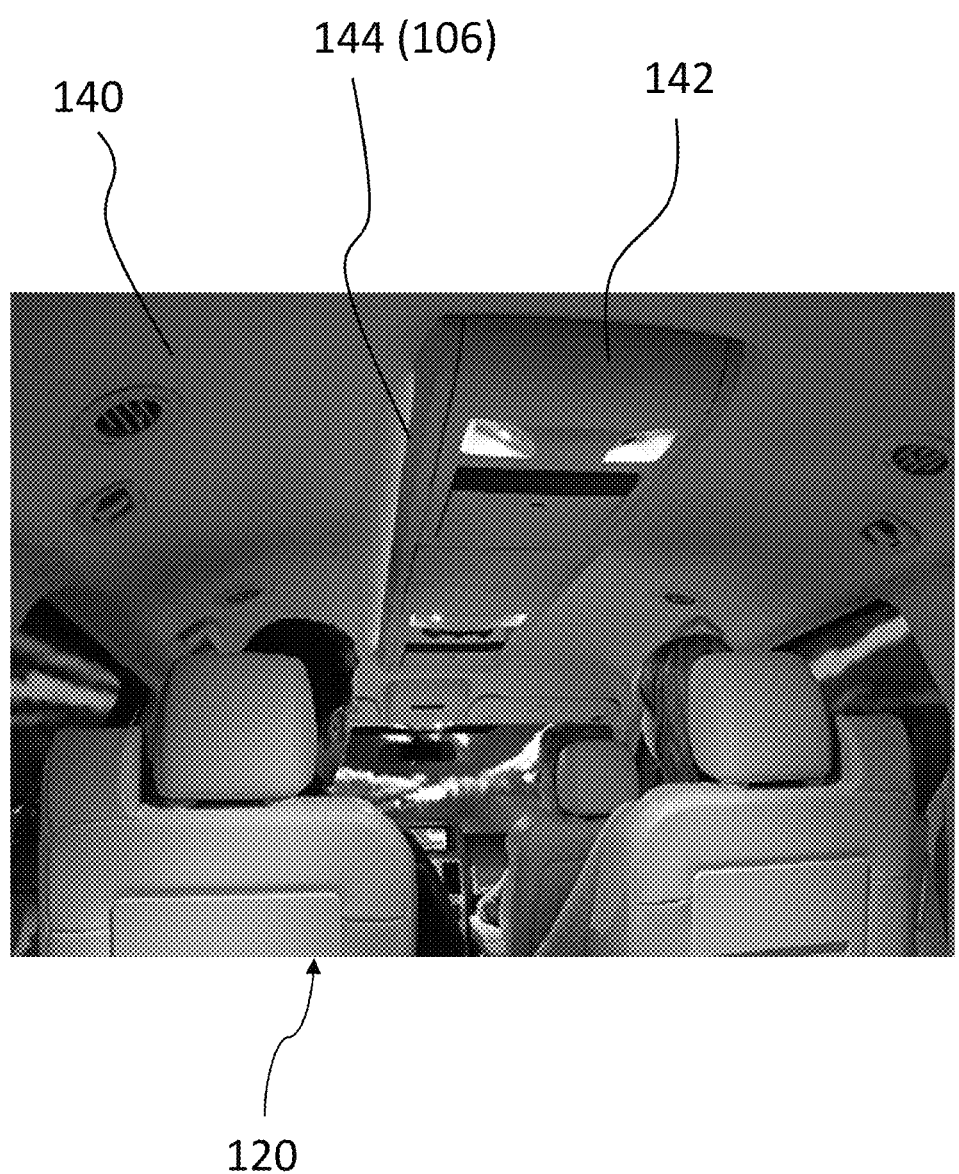
FIG. 12 is an illustration of an exemplary embodiment of a lighting system in a vehicle.
Figure 13:
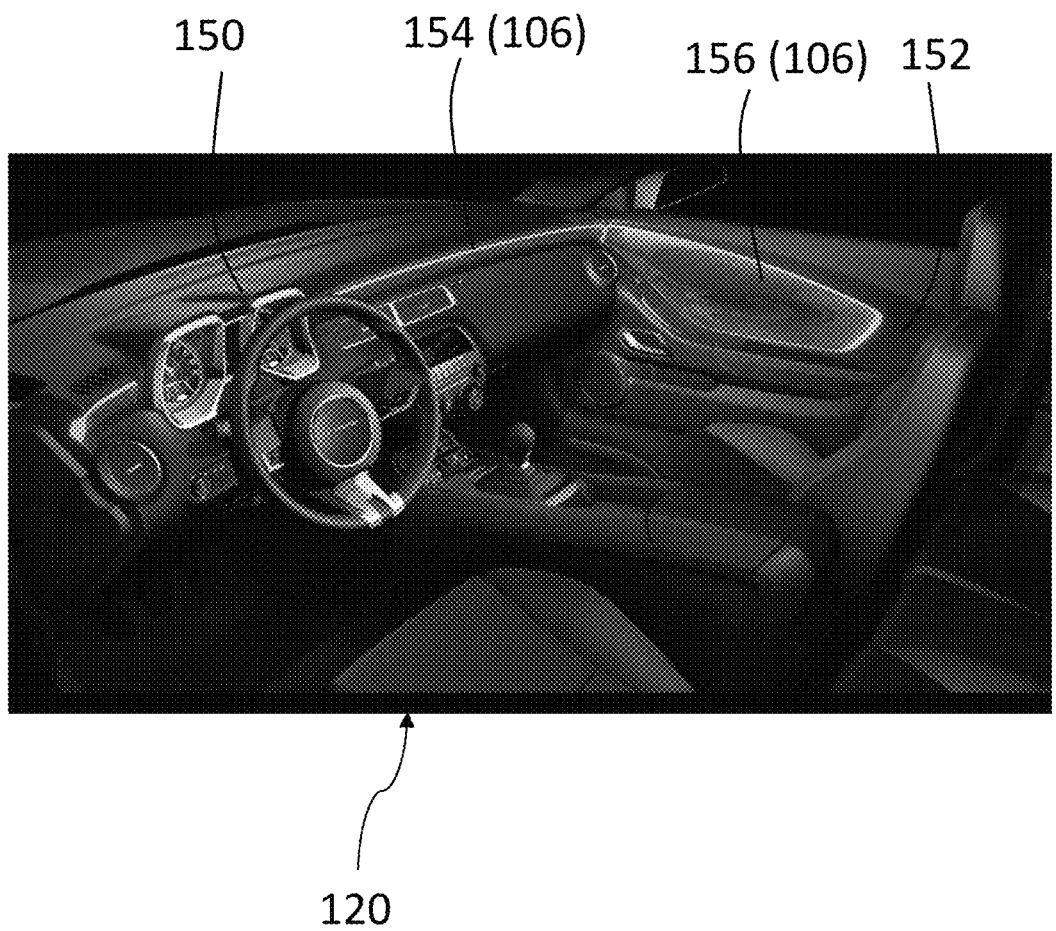
FIG. 13 is an illustration of an exemplary embodiment of a lighting system in a vehicle.

FIGS. 12 and 13 are illustrations showing additional exemplary embodiments of subliminal sensory system 106 implemented as a lighting system 144. For example, FIG. 12 shows an exemplary embodiment in which a lighting system 144 is incorporated into an overhead console 142 provided on a ceiling 140 of a vehicle 120. FIG. 13 shows an exemplary embodiment in which a lighting system 154, 156 is incorporated into a dashboard 150 and side panel 152 of a vehicle 120.

Figure 14:
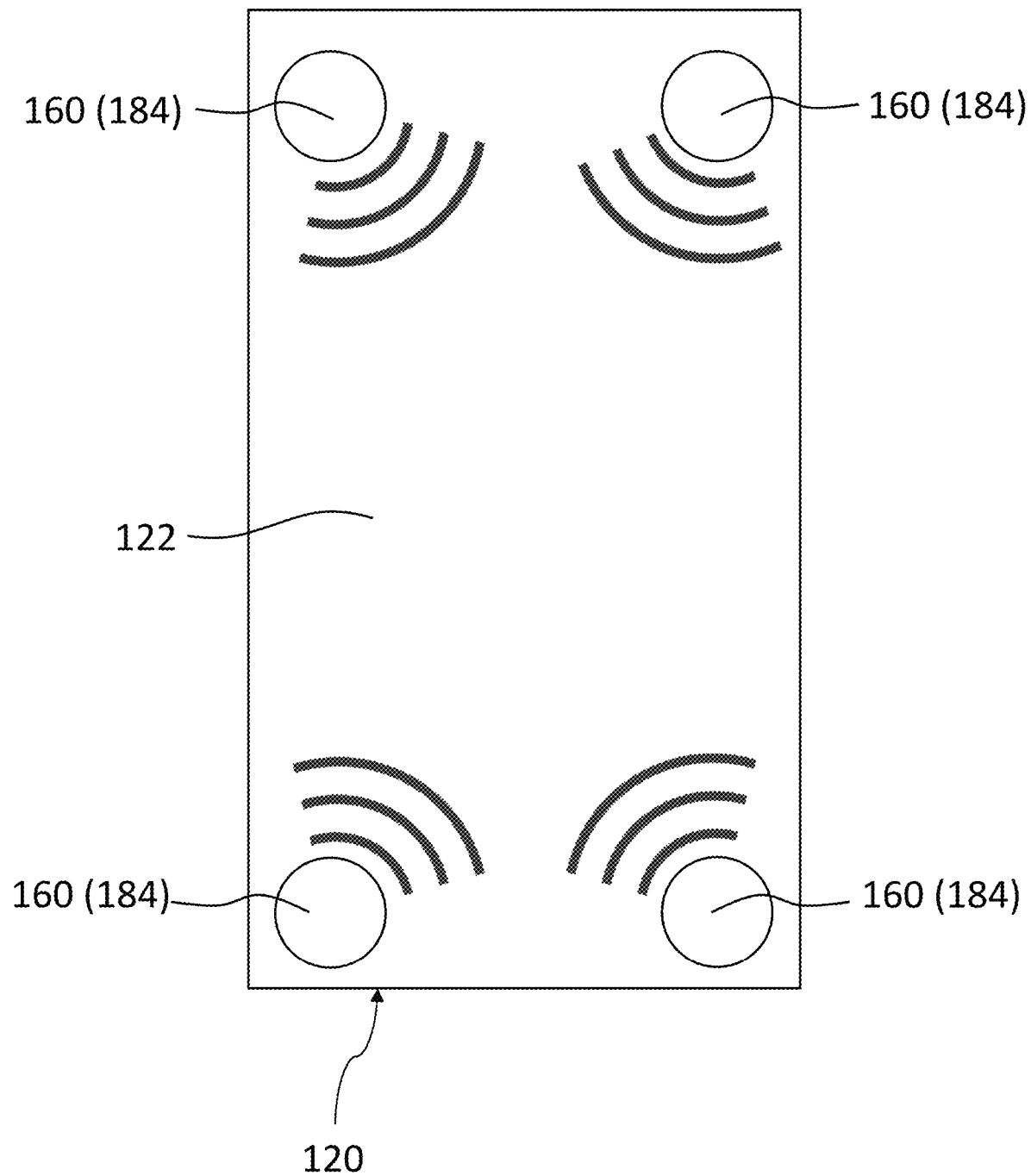
FIG. 14 is a schematic diagram of an exemplary embodiment of a sound system in a vehicle.
Figure 15:
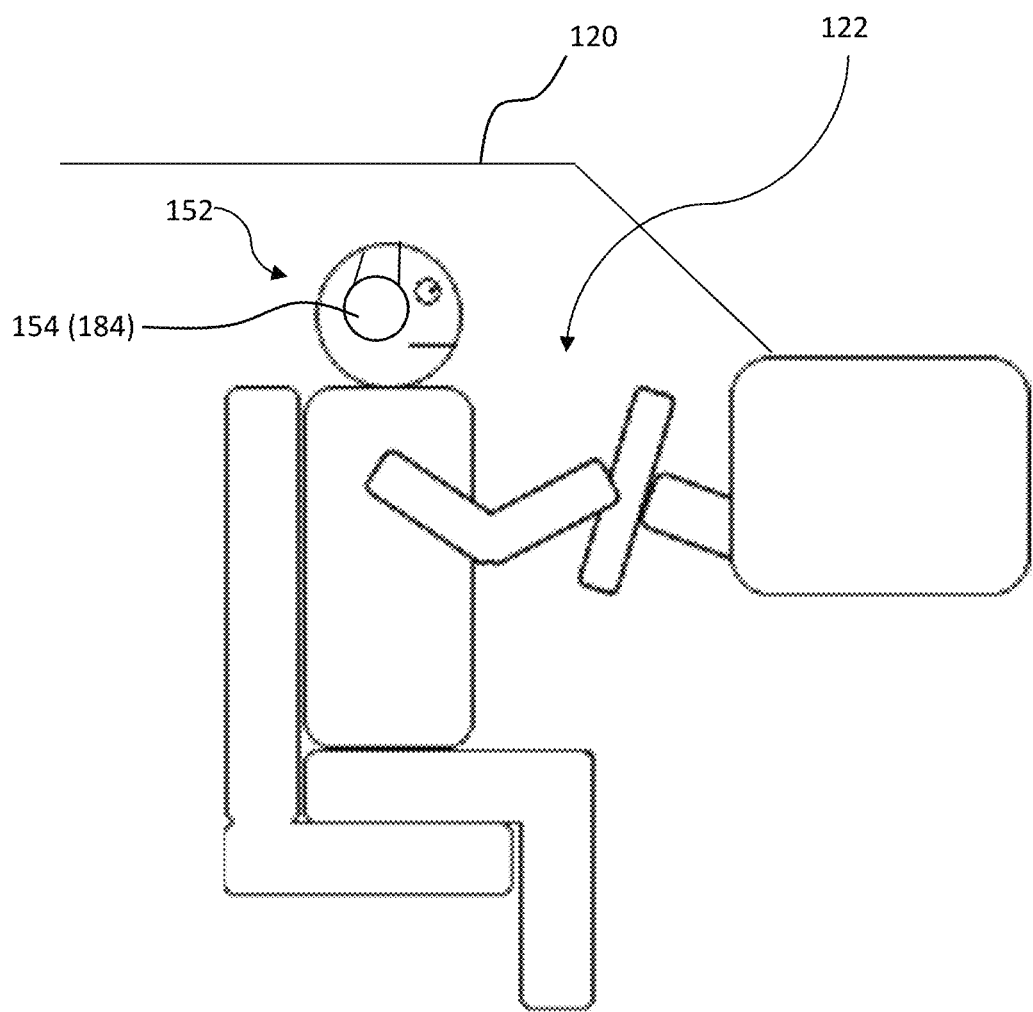
FIG. 15 is a schematic diagram of an exemplary embodiment of a sound system in a vehicle.
Figure 20:
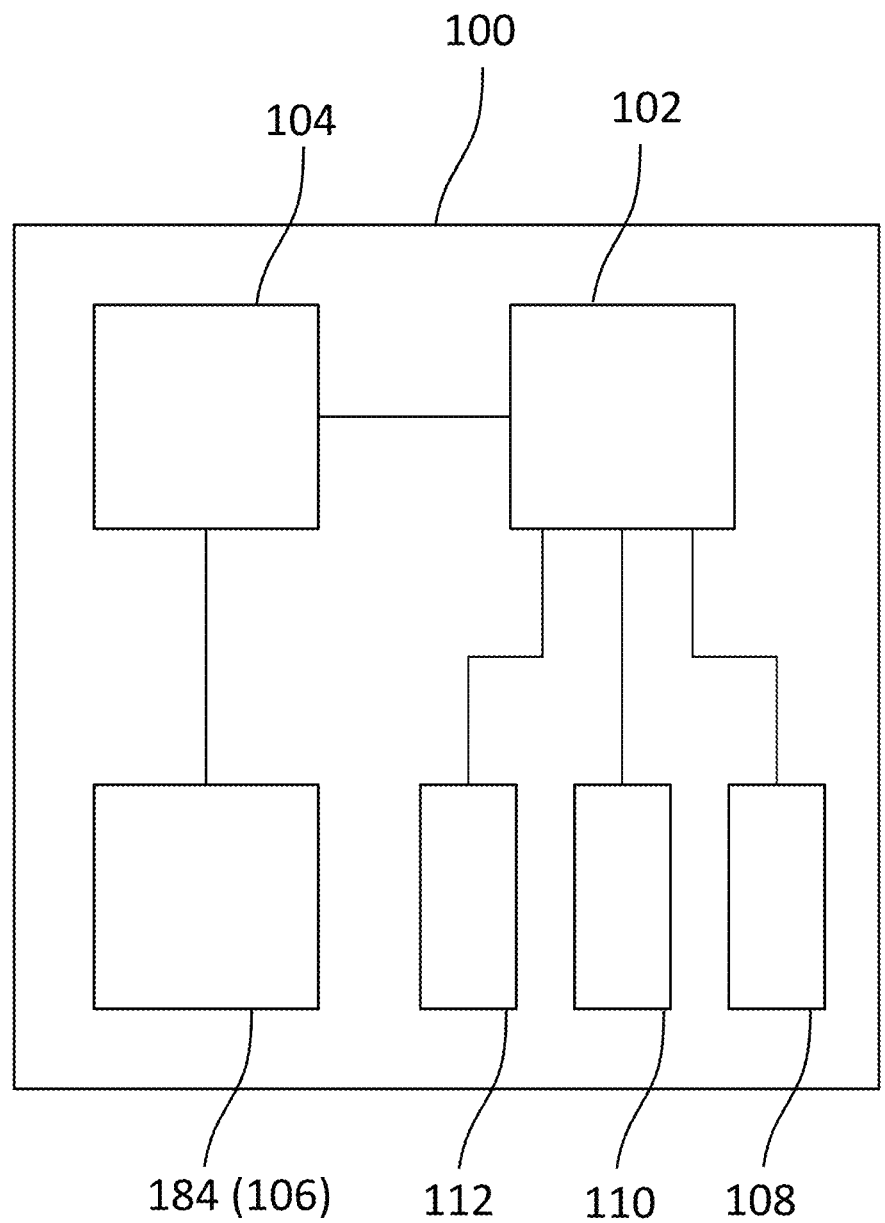
FIG. 20 is a schematic diagram illustrating an exemplary embodiment of a system for promoting passenger trust and mitigating motion sickness in a vehicle.

In addition to the lighting system 182 described herein, subliminal sensory system 106 may be implemented as a sound system 184 provided in an interior cabin 122 of vehicle 120, as seen in FIG. 20. FIG. 14 shows an exemplary embodiment in which the sound system 184 is implemented as a system of speakers provided in an interior cabin 122 of vehicle 120. FIG. 15 shows an exemplary embodiment in which the sound system 184 is implemented as a personal sound device 154 worn by passenger 152. Personal sound device 154 may comprise headphones, earphones, ear buds, or similar devices. Personal sound device may be in wireless communication with processor 104 (see FIG. 1).

Processor 104 (see FIG. 1) may be configured to control pitch, volume, and apparent origin of an output of sound system 184 to provide an audible representation of an anticipated or imminent force on a passenger. The default output of sound system 184 could be a white noise or similarly non-intrusive ambient noise. As the vehicle 120 is operated, sound system 184 may be controlled such that the apparent direction of the source of the sound output can be moved corresponding to apparent or imminent force to be felt by passenger 152. For example, if vehicle 120 brakes, processor 104 may control sound system 184 such that the apparent origin of the source of the sound output is toward the front of vehicle 120. If vehicle 120 accelerates, processor 104 may control sound system 184 such that the apparent origin of the source of the sound output is toward the rear of vehicle 120. If vehicle 120 turns, processor 104 may control sound system 184 such that the apparent origin of the source of the sound output moves to an outside of the turn of vehicle 120. As an alternative exemplary embodiment, the output of sound system 184 may be controlled by processor 104 to mimic a sound of fluid flowing in a direction of an apparent force on the passengers, similar to how lighting system 182 is controlled to mimic the appearance of flowing fluid as described above.

In an exemplary embodiment, processor 104 (see FIG. 1) may control pitch, volume, and apparent origin of an output of sound system 184 to inform passenger 152 of a driving environment based on an output of second sensor 190, such as a passing car. For example, processor 104 may control sound system 184 to output the sound of a passing vehicle, and an apparent direction of the source of the sound may move as the position of the passing vehicle changes relative to vehicle 120.

Figure 16:
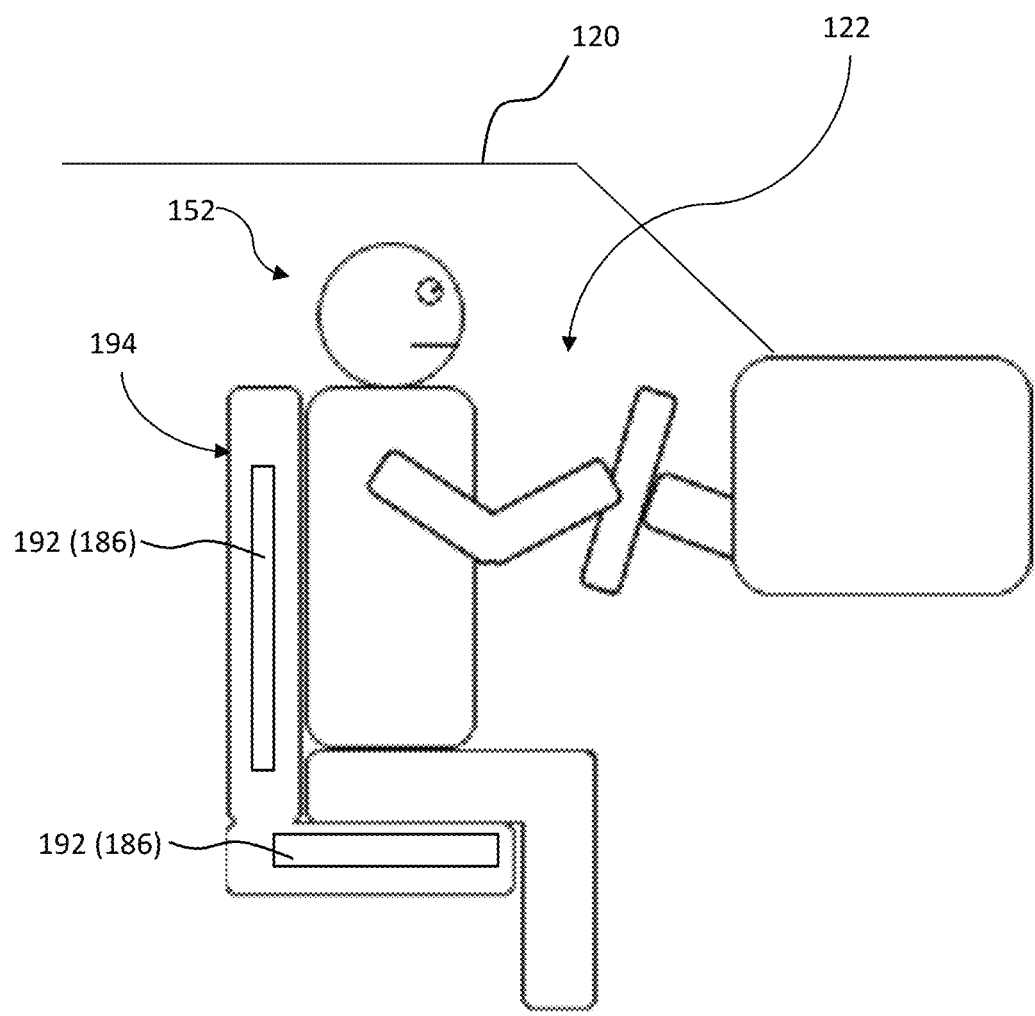
FIG. 16 is a schematic diagram of an exemplary embodiment of a haptic system in a vehicle.
Figure 21:
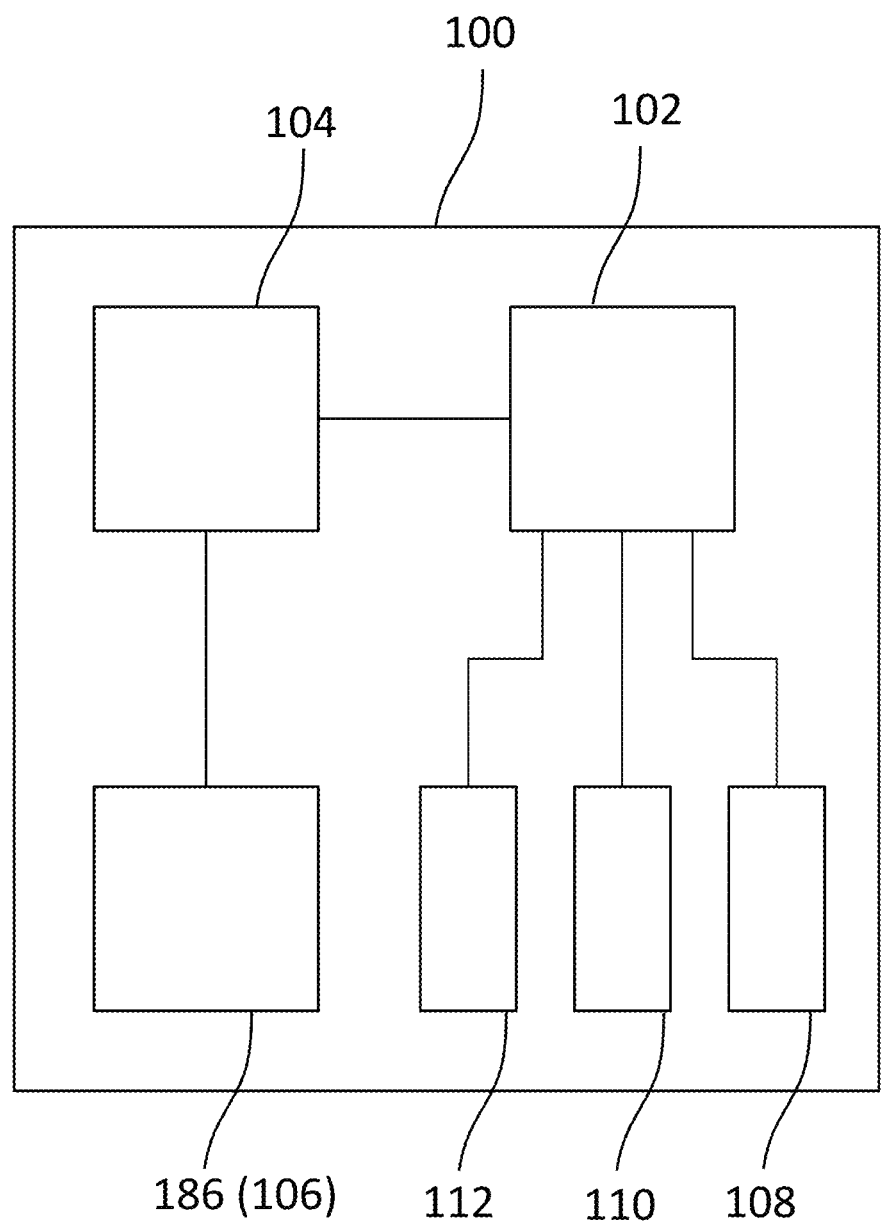
FIG. 21 is a schematic diagram illustrating an exemplary embodiment of a system for promoting passenger trust and mitigating motion sickness in a vehicle.

In addition to the lighting system 182 and sound system 184 described above, subliminal sensory system 106 may be implemented as a haptic system 186 provided in an interior cabin 122 of vehicle 120, as seen in FIG. 21. FIG. 16 shows an exemplary embodiment in which haptic system 186 is implemented as a stimulation device 192 provided in a seat 194 of vehicle 120. Stimulation device 192 may be a vibration device or actuator structured to provide haptic or tactile output to passenger 152. Stimulation device 192 may be structured to selectively provide output at specific positions on seat 194, such as to the front, rear, or left and right sides of seat 194.

In an exemplary embodiment, processor 104 (see FIG. 1) may control stimulation device 192 to provide information about the operational status of vehicle 120 to passenger 152. For example, if vehicle 120 brakes, processor 104 may control stimulation device 192 to create small vibrations or tactile pressure moving from a rear of seat 194 toward a front of seat 194. If vehicle 120 accelerates, processor 104 may control stimulation device 192 to create small vibrations or tactile pressure moving from the front of seat 194 toward the rear of seat 194. If vehicle 120 turns, processor 104 may control stimulation device 192 to create small vibrations or tactile pressure moving from a center of seat 194 toward a side of seat 194 corresponding to an outside of the turn. It will be understood that the vibration or tactile output produced by stimulation device 192 may be set at a minimal intensity so as to provide subliminal, subconscious, or precognitive awareness of the vibration or tactile output.

In an exemplary embodiment, processor 104 (see FIG. 1) may operate stimulation device 192 to inform passenger 152 of a driving environment based on an output of second sensor 190 (see FIG. 18), such as a passing car. For example, processor 104 may control stimulation device 192 to provide a vibration or tactile output at a position on seat 194 corresponding to a position of the passing car relative to vehicle 120.

While passenger 152 is shown as a driver of vehicle 120, it will also be understood that subliminal sensory system 106 can be perceived by, and affect other passengers, in the vehicle 120. For example, lighting system 182 may be perceived by any passengers in an interior cabin 122 of vehicle 120, speakers 160 may be heard by an passenger in an interior cabin of the vehicle, and all seats of the vehicle may be equipped with stimulation devices 192. In the embodiments described above, processor 104 controls subliminal sensory system 106 to provide a visual, audible, or haptic representation of an anticipated or imminent force on passenger 152. Thus, even if the passenger is not actively aware of the operation of the vehicle (i.e., reading a book, operating a personal device, having a conversation), output of subliminal sensory system 106 will provide a subliminal, subconscious, or precognitive indication of the operation of the vehicle to the passenger. In this way, the apparent force felt by passengers will be more closely aligned with their sensory perceptions, thereby increasing passenger trust in the operation of the vehicle, reduction of passenger anxiety, and reduced incidence of motion sickness.

Additionally, the intensity and levels of the visual, audible, or haptic sensations provided by subliminal sensory system 106 may be selected so as to be minimally intrusive to the passenger's cognition. For example, light intensity, sound volume, or haptic intensity may be set to levels that may be subliminally perceived by a passenger, but are not so intense so as to startle the passenger or capture their active attention.

Subliminal sensory system 106 may also include more than one of lighting system 182, sound system 184, and haptic system 186 implemented together. In this way, subliminal sensory system 106 can provide information through a variety of alternative senses, thereby allowing the benefits of the system to be enjoyed by passengers who may have impairment of a particular sense.

Figure 17:
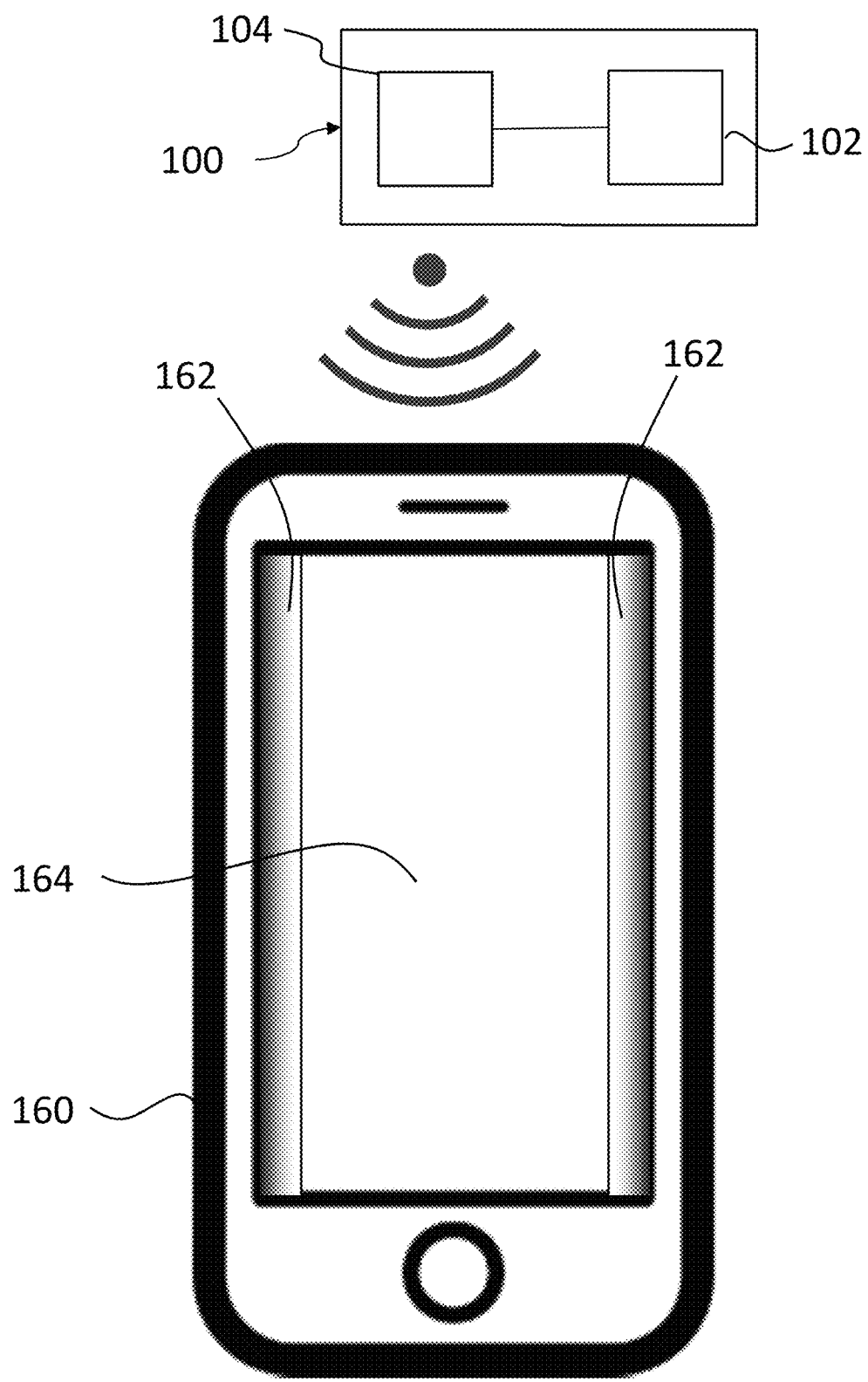
FIG. 17 is a schematic diagram of an exemplary embodiment of a system in conjunction with a personal electronic device.

FIG. 17 shows an exemplary embodiment of a system 100 for promoting passenger trust and mitigating motion sickness in a vehicle that may operate in conjunction with a personal electronic device 160 of a passenger. Processor 104 may be configured to wirelessly communicate with personal electronic device 160 and control the personal electronic device to show a graphic 162 in a peripheral area of a display 164. Shape, color, size, and motion of graphic 162 can be controlled by processor 104 to subliminally provide information about the operational status of the vehicle to the passenger, such as information about anticipated or imminent forces experienced by the passenger due to braking, acceleration, or turning, or information about a driving environment such as nearby objects, similar to the function of lighting system 182 described in detail above.

Figure 22:
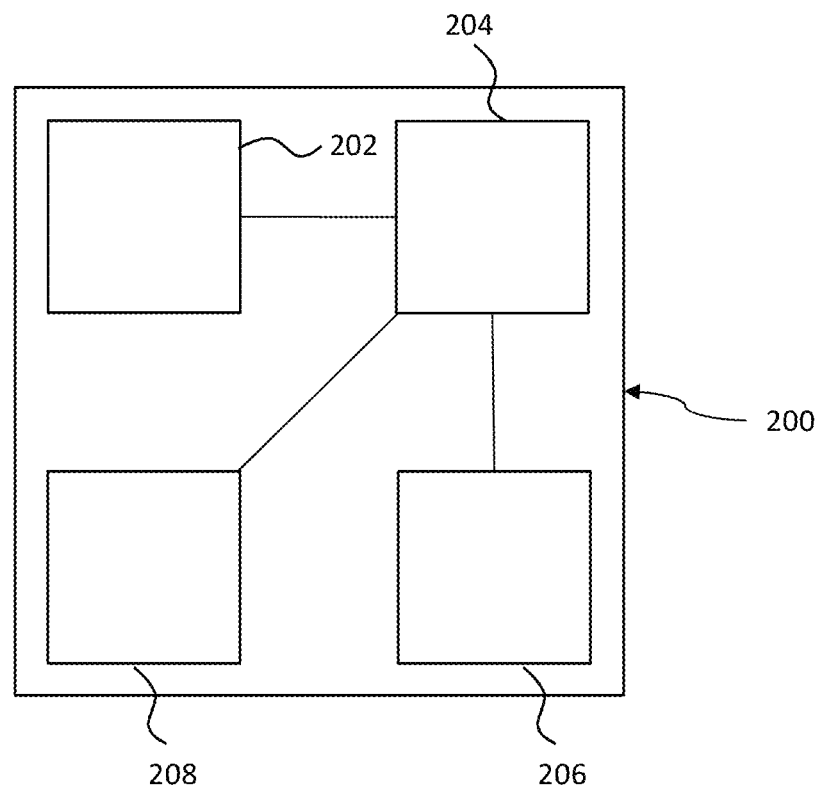
FIG. 22 is a schematic diagram illustrating an exemplary embodiment of a system for promoting passenger trust and mitigating motion sickness in a vehicle.

In another exemplary embodiment, a system for promoting passenger trust and mitigating motion sickness may be implemented in a vehicle having an automated driving system. For example, FIG. 22 shows a system 200 having a first sensor 202, a processor 204, an automated driving system 206, and a subliminal sensory system 208. Processor 204 may be operably connected to first sensor 202, automated driving system 206, and subliminal sensory system 208. First sensor may detect a driving environment of the vehicle as described in detail above. Alternatively, first sensor 202 may be implemented as a part of, or a subsystem of, automated driving system 206. Automated driving system 206 may include, or be operably connected to, various sensors for detecting a driving environment and various controllers for controlling speed, acceleration, braking, and steering of the autonomous vehicle based on a vehicle path plan calculated by processor 204. The vehicle path plan may include a series of maneuvers planned for an autonomous vehicle based on a desired destination and the local driving environment.

Subliminal sensory system 208 may be any one of, or any combination of, a lighting system 182, a sound system 184, and a haptic system 186 described in detail herein. Processor 204 may control subliminal sensory system 208, based on the vehicle path plan, to provide subliminal information to the passengers regarding upcoming maneuvers or the driving environment. In operation, subliminal sensory system 208 is similar to the operation of subliminal sensory system 106 described herein, except that subliminal sensory system 208 is providing information based on a calculated vehicle path plan instead of real time operation data of the vehicle. This provides a benefit to the passengers in that the subliminal information provided by subliminal sensory system 208 matches or anticipates apparent forces felt by passengers in the autonomous vehicle, thereby enhancing passenger trust in the operation of autonomous vehicle and reducing possible motion sickness.

While the above disclosure has been described with reference to exemplary embodiments, it will be understood by those skilled in the art that various changes may be made and equivalents may be substituted for elements thereof without departing from its scope. In addition, many modifications may be made to adapt a particular situation or material to the teachings of the disclosure without departing from the essential scope thereof. Therefore, it is intended that the present disclosure not be limited to the particular embodiments disclosed, but will include all embodiments falling within the scope thereof

What is claimed is:

1. A system for promoting trust of a passenger not actively aware of vehicle operation for use in conjunction with a hand held personal electronic device of the passenger, the system comprising:
   a first sensor structured to detect an operational status of the vehicle; and
   a processor operably coupled to the first sensor;
   wherein the processor is structured to wirelessly communicate with the hand held personal electronic; device including a display and control the hand held personal electronic device of the passenger to provide information about the operational status of the vehicle including anticipated forces on the vehicle and activities outside of the vehicle to the passenger not actively aware of vehicle operation, and
   wherein the processor is structured to control the display of the hand held personal electronic device of the passenger to show a graphic around an outer periphery of the display and control one of color, intensity, and apparent motion of the graphic to provide a visual representation of an object proximate to the vehicle based on the driving environment detected by the second sensor to build trust in autonomous vehicle operation with the passenger not actively aware of the vehicle operation.

2. The system of claim 1, wherein the processor is structured to control the display of the hand held personal electronic device of the passenger to show a graphic around an outer periphery of the display; and the processor is structured to control the color, the intensity, or the apparent motion of the graphic to provide a visual representation of an anticipated force on the passenger.

3. The system of claim 1, wherein the processor is structured to control a sound system coupled to the hand held personal electronic device of the passenger and adjust pitch, volume, or apparent origin of an output of the sound system to provide information about the operational status of the vehicle to further promote trust in vehicle operation with the passenger not actively aware of the vehicle operation.

* * * * *